(12) United States Patent
Wong et al.

(10) Patent No.: US 6,316,028 B1
(45) Date of Patent: *Nov. 13, 2001

(54) BANDED PROLONGED RELEASE ACTIVE AGENT DOSAGE FORM

(76) Inventors: Patrick S.-L. Wong; David Emil Edgren; Liang C. Dong, all of P.O. Box 7210, Mountain View, CA (US) 94039-7210; Vincent Joseph Ferrari, 161 Trimaran Ct., Foster City, CA (US) 94404

(*) Notice: Subject to any disclaimer, the term of this patent is extended or adjusted under 35 U.S.C. 154(b) by 0 days.

This patent is subject to a terminal disclaimer.

(21) Appl. No.: 09/652,655

(22) Filed: Aug. 31, 2000

Related U.S. Application Data

(63) Continuation of application No. 09/448,821, filed on Nov. 24, 1999, now abandoned, which is a continuation of application No. 09/149,042, filed on Sep. 8, 1998, now Pat. No. 6,020,000, which is a continuation of application No. 08/899,683, filed on Jul. 24, 1997, now abandoned, which is a continuation of application No. 08/671,226, filed on Jun. 27, 1996, now Pat. No. 5,667,804, which is a continuation of application No. 08/394,074, filed on Feb. 24, 1995, now Pat. No. 5,534,263.

(51) Int. Cl.[7] .................................................... A61K 9/24

(52) U.S. Cl. ........................ 424/473; 424/484; 424/486

(58) Field of Search .................................. 424/472, 473, 424/471, 474, 467, 486, 468, 484

(56) References Cited

U.S. PATENT DOCUMENTS

| | | |
|---|---|---|
| 4,290,426 | 9/1981 | Luschen et al. . |
| 4,327,725 | 5/1982 | Cortese et al. . |
| 4,503,031 | 3/1985 | Glassman . |
| 4,792,448 | 12/1988 | Ranade . |
| 4,803,076 | 2/1989 | Ranade . |
| 4,824,677 | 4/1989 | Shah et al. . |
| 4,839,177 | 6/1989 | Colombo et al. . |
| 4,915,950 | 4/1990 | Miranda et al. . |
| 5,023,088 | 6/1991 | Wong et al. . |
| 5,256,440 | 10/1993 | Appel et al. . |
| 5,266,332 | 11/1993 | Dong et al. . |
| 5,326,570 | 7/1994 | Rudnic et al. . |
| 5,422,123 | 6/1995 | Conte et al. . |

(List continued on next page.)

FOREIGN PATENT DOCUMENTS

| | | |
|---|---|---|
| 99/18938 | 4/1999 | (WO) . |
| 99/21551 | 5/1999 | (WO) . |

OTHER PUBLICATIONS

Robert Langer et al., Polymers for the Controlled Release of Macromolecules: Kinetics, Applications and External Control, AIChE Symposium Series, No. 206, vol. 77, 1981, pp. 10–20.

Dean S.T. Hsieh et al., Zero–Order Controlled–Release Polymer Matrices for Micro—and Macromolecules, Journal of Pharmaceutical Sciences, vol. 72, No. 1, Jan. 1983, pp. 17–22.

U. Conte et al., Journal of Controlled Release, 26 (1993), pp. 39–47, "Multi–Layered hydrophilic matrices as constant release devices".

Robert H. Zimmer, M.D., Ph.D., "How to Develop Drug Products Using the Geomatrix Technology," JAGO Pharma AG, Apr. 1997.

*Primary Examiner*—Thurman K. Page
*Assistant Examiner*—Rachel M. Bennett

(57) ABSTRACT

The present invention is directed to an active agent dosage that is useful for the prolonged delivery of an active agent formulation to fluid environment of use. The active agent dosage form is a matrix that has an insoluble material circumscribing a portion of the surface of the matrix. The invention is also directed to a method of making the active agent dosage form.

18 Claims, 4 Drawing Sheets

U.S. PATENT DOCUMENTS

| | | |
|---|---|---|
| 5,464,633 | 11/1995 | Conte et al. . |
| 5,487,901 | 1/1996 | Conte et al. . |
| 5,534,263 * | 7/1996 | Wong et al. ................ 424/473 |
| 5,626,874 | 5/1997 | Conte et al. . |
| 5,629,008 | 5/1997 | Lee . |
| 5,650,169 | 7/1997 | Conte et al. . |
| 5,667,804 | 9/1997 | Wong et al. . |
| 5,738,874 | 4/1998 | Conte et al. . |
| 5,780,057 | 7/1998 | Conte et al. . |
| 6,020,000 | 2/2000 | Wong et al. . |

* cited by examiner

BANDED PROLONGED RELEASE ACTIVE AGENT DOSAGE FORM

This application is a continuation of application Ser. No. 09/448,821 (now abandoned) filed Nov. 24, 1999, which is a continuation of application Ser. No. 09/149,042, filed Sep. 8, 1998 (now U.S. Pat. No. 6,020,000), which is a continuation of application Ser. No. 08/899,683, filed Jul. 24, 1997, (now abandoned) which is a continuation of application Ser. No. 08/671,226, filed Jun. 27, 1996 (now U.S. Pat. No. 5,667,804), which is a continuation of application Ser. No. 08/394,074, filed Feb. 24, 1995 (now U.S. Pat. No. 5,534,263).

FIELD OF THE INVENTION

The present invention is related to the prolonged delivery of an active agent. More particularly, it is a banded active agent dosage form useful for delivering a beneficial agent to a fluid environment of use. The invention is also directed to the method of making the banded active agent dosage form.

BACKGROUND OF THE INVENTION

Tablets, capsules, caplets and many other types of devices have been used for dispensing a beneficial agent to a fluid environment of use. Easy manufacture of a device that provides for prolonged delivery of an active agent in a controlled and predictable manner continues to be a goal, especially in the area of drug delivery.

U.S. Pat. No. 4,290,426 to Luschen et al describes a cylindrical dispenser for releasing a beneficial agent into a fluid environment at a rate that is governed by the fluid induced relaxation of a polymeric agent contained within the dispenser. The cylindrical dispenser includes an impermeable container that has within it a reservoir and a passageway from the reservoir to the exterior of the container. The reservoir contains a polymer and a beneficial agent. The polymer imbibes fluid from the environment and thereby undergoes relaxation, releasing the beneficial agent from the device. The amount of agent released is dependent on the rate of relaxation of the polymer over time.

Coated dosage forms have also been suggested for delivery of a controlled amount of a beneficial agent over a prolonged period of time. U.S. Pat. No. 5,256,440 describes a process for producing a film coated dosage form. A continuous groove is inscribed in a dosage form core. A latex film is coated onto the core, the groove defining a fixed zone and a detachable zone for the film. The detachable portion of the latex film detaches when it is exposed to the environment of use, thereby exposing a discrete portion of the dosage from core surface. The remainder of the film remains attached to the dosage form core. The exposed portion of the dosage form surface erodes and releases active agent to the environment of use.

Coated tablets for constant and prolonged drug release are described by Conte et al in *J. Controlled Release,* Vol. 26, (1993) pages 39–47. These GEOMATRIX™ Systems are swellable matrices that are coated or tableted with polymeric barrier layers. Release performances of the systems are modulated as a result of the restriction of the releasing surface by the polymeric barrier layer coatings. As the extent of coating of the system's surface is increased, the release of kinetics of the system shift toward constant release. These systems are further described in U.S. Pat. No. 4,839,177 to Colombo et al.

As can be observed in the above-referenced patents and publications, devices have been described that provide for prolonged delivery of an active agent. However, there remains a continuing need for improved systems for delivering an active agent in a reliable and reproducible manner that are easy and inexpensive to manufacture.

SUMMARY OF THE INVENTION

We have observed that devices such as those described above will provide for prolonged delivery of an active agent formulation to a fluid environment of use but that these devices may not necessarily provide for controlled and reliable release. Accordingly, the present invention is directed to a dispensing device that will release an active agent in formulation in a reliably controllable manner, and further that is easy and inexpensive to manufacture.

The invention is directed to an active agent dosage form for the prolonged delivery of an active agent to a fluid environment of use. The surface of an active agent formulation matrix contains two or more insoluble bands.

In one aspect, the invention is directed to an active agent dosage form for the prolonged delivery of an active agent to a fluid environment of use. Two or more insoluble bands surround an active agent formulation matrix. The bands drop off the matrix as it erodes, providing a decreasing path length for delivery of the drug.

In another aspect, the invention is to an active agent dosage form for the prolonged delivery of an active agent to a fluid environment of use where two or more insoluble bands are printed or otherwise securely affixed to the surface of the dosage form. The surface area of the matrix between the bands erodes delivering active agent to the fluid environment of use. The surface area not covered by the rings increases with time.

The invention is also directed to a method for preparing the active agent dosage form for prolonged delivery of an active agent. An active agent formulation matrix is prepared and insoluble material is placed or printed onto the formulation to form two or more insoluble bands on the surface of the matrix.

DESCRIPTION OF THE DRAWINGS

The figures are not drawn to scale, but are set forth to illustrate various embodiments of the invention. Like numbers refer to like structures.

DETAILED DESCRIPTION OF THE INVENTION

The present invention provides a device that is useful for the prolonged delivery of an active agent formulation to a fluid environment of use.

Definitions

The phrase "prolonged delivery" intends a period of delivery that lasts for several hours to about 24 hours, usually up to about 20 hours, and often between 3 and 16 hours.

By "insoluble" is intended a material that will not dissolve, degrade or erode in the environment of use during the delivery period.

By "apply" or "applied" or "application" intends the substantially uniform deposition of insoluble material, in liquid or in molten form, onto the active agent formulation matrix. A variety of techniques may be used to apply the insoluble material, including but not limited to Gravure-type printing, extrusion coating, screen coating, spraying, painting, and the Capsealer process developed by TAIT Design & Machine Co., Manheim, Pa.

The term "active agent formulation" intends the active agent or drug optionally in combination with pharmaceutically acceptable carriers and additional inert ingredients.

The term "active agent formulation matrix", as used herein, comprises the active agent formulation in combination with a hydrophillic polymeric material.

The term "active agent dosage form" intends the active agent formulation matrix as defined above with two or more bands of an insoluble material applied onto its surface.

As used heein, the terms "Therapeutically effective" amount or rate refer to the amount or rate of the active agent needed to effect the desired pharmacologic, often beneficial, result.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

Figure 1:
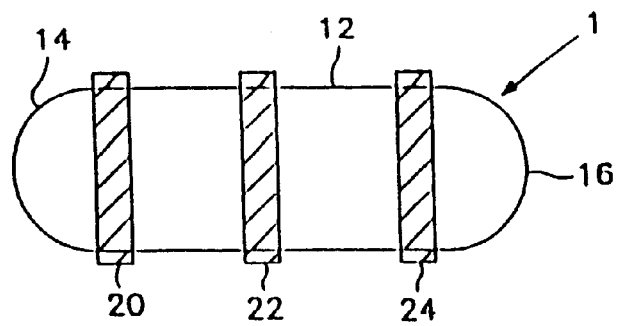
FIG. 1 is a side elevational view of one embodiment of the delivery device of the present invention, the device being in prepared form prior to placement in the environment of use.

FIG. 1 depicts, in side elevational view, one embodiment of the delivery device according to the present invention. The device is shown in prepared form prior to placement in the environment of use. Dispensing device 1 is shown in FIG. 1 to comprise a cylindrically shaped active agent formulation matrix 12. The ends 14 and 16 of the matrix are preferably rounded and convex in shape in order to ensure ease of insertion into the environment of use. Bands 20, 22, and 24 concentrically surround the cylindrical matrix 12.

Figure 2:
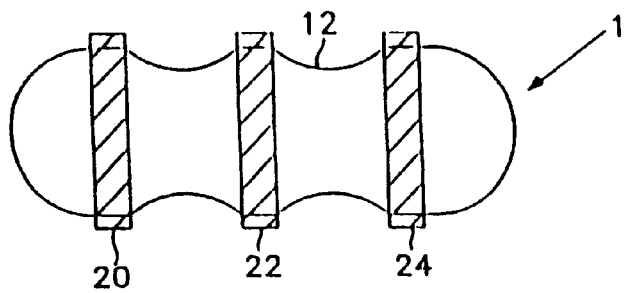
FIG. 2 shows the device of FIG. 1 in operation after placement in the environment of use, showing erosion of the active agent formulation matrix.

FIG. 2 shows dispensing device 1 in operation after having been placed in the fluid environment of use. The active agent formulation matrix 12 between bands 20, 22 and 24 has begun to erode, thereby releasing active agent to the fluid environment of use.

Figure 3:
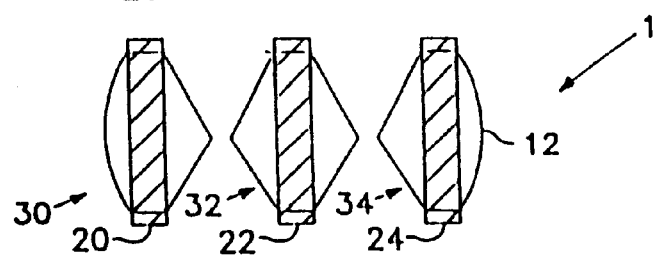
FIG. 3 shows the device of FIG. 1 in operation after sufficient erosion of the matrix has caused separation of the banded sections of the device.

FIG. 3 shows dispensing device 1 in operation after a length of time in the fluid environment of use. The active agent formulation matrix 12 has eroded between bands 20, 22 and 24 to such an extent that the lmatrix 12 is now in three pieces, 30, 32 and 34. Erosion will continue until the matrix portions of each of the pieces have completely eroded. Bands 20, 22 and 24 will thereafter be expelled from the fluid environment of use.

Figure 4:
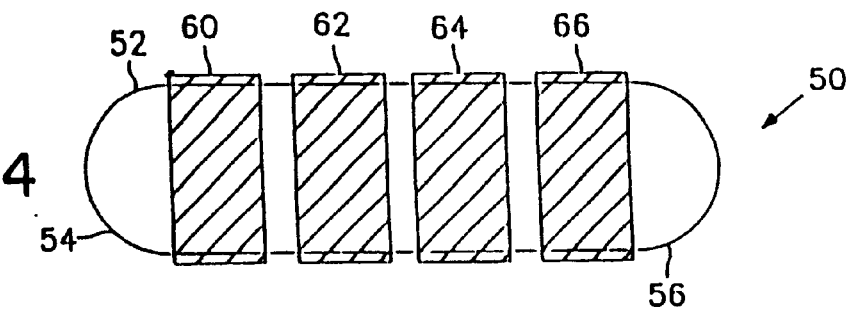
FIG. 4 is a side elevational view of a second embodiment of the delivery device of the present invention, the device being in prepared form prior to placement in the environment of use.

FIG. 4 shows, in side elevational view, a second embodiment of the delivery device according to the present invention. The device is shown in prepared form prior to placement in the environment of use. Dispensing device 50 comprises a cylindrically shaped active agent formulation matrix 52 with convex ends 54 and 56. Bands 60, 62, 64 and 66 concentrically surround the cylindrical matrix 52.

Figure 5:
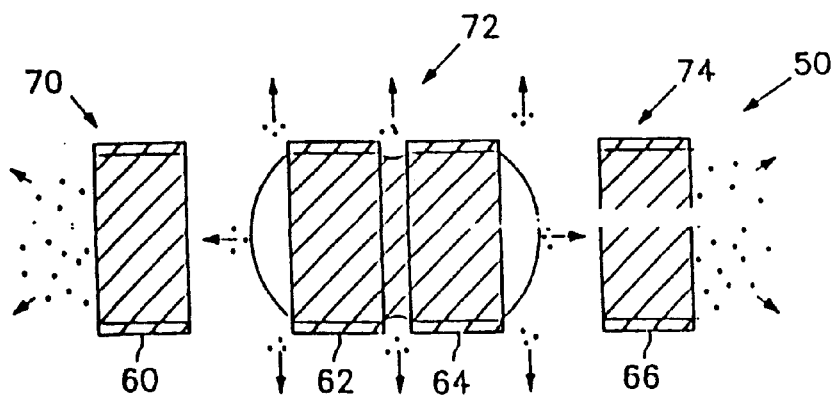
FIG. 5 shows the device of FIG. 4 in operation after sufficient erosion of the matrix has caused separation of the sections of the device.

FIG. 5 shows dispensing device 50 in operation after a length of time in the fluid environment of use. The active agent formulation matrix 52 has eroded from the exposed ends of bands 60, and 66 to such an extent that the device 50 is now in three pieces, 70, 72, and 74. The arrows show the erosion of the matrix and therefore the extent of active agent delivery. Erosion will continue from the exposed ends of bands 62 and 64 until the matrix has completely eroded. Bands 60, 62, 63 and 66 will thereafter be expelled from the fluid environment of use.

The active agent itself may be in liquid, solid or semisolid form. The active agent formulation may contain additional materials and may be designed in a multitude of ways to provide a specific drug delivery profile. One embodiment comprises a formulation that contains a biologically acceptable hydrophillic polymer which is capable of slow dispersion in the environment fluid. In another embodiment, the formulation may contain a hydrophillic polymer and a surfactant so that the formulation is susceptible to erosion in the environment. In still another embodiment, the formulation may include a solid surfacant and provide drug delivery in a finely dispersed form. In yet a further embodiment, the formulation may include coated microspheres of an active agent and an adjuvant. The active agent and adjuvant can be delivered simultaneously from the microspheres either by diffusion or by osmosis. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some pharmacologic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, indcluding, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins. lipoproteins, polypepticides, steroids, hypnotics and sedatives, psychic energizers, tranquilizers, anticonvulsants, muscle relaxants, antiparkinson agents, analgesics, antiinflammatories, local anesthetics, muscle contractants, antimicrobials, antimalarials, hormonal agents including contraceptives, sympathomimetics, polypeptides and proteins capable of eleciting physiological effects, diuretics, lipid regulating agents, antiandrogenic agents, antiparasitics, neoplastics, hypoglycemics, nutritional agents and supplements, growth supplements, fats, ophthalmics, antienteritis agents, electrolytes and diagnostic agents.

Examples of beneficial agents useful in this invention include prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, theithylperazine maleate, anisindione, diphenadione erythrityl tetranitrate, digoxin, insoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone. hydrocorticosterone acetate, cortisone acetate,dexamethasone and its derivatives such as betamethasone, tramcinolone, methyitestosterone, 17 β-estradiol, ethinyl estradiol, ethinyl estradiol 3-methyl ether, prednisolone, 17-β-hydroxyprogesterone acetate, 19-nor-progesterone, norgestrel, norethindrone, norethisterone, norethiederone, progesterone, norgesterone, norethynodrel, aspirin, actaminophen, indomethacin, naproxen, fenoprofen, sulindac, indoprofen, nitreoglycerin, issorbide dinitrate, propranolol, timolol, atenolol, alprenolol, cemetidine, clonidine, imipramine, levodopa, chlorpromazine, methyldopa, dihydroxphenylalanine, calcium gluconate, ketroprofen, ibuprofen, cephalexin, erthromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amiodipine, mioflazine, lisinopril, enalpril, captopril, remipril, enalaprilat, famotidine, nizatidine, sucralfate, etintidine, tetratolol, minoxidil, chloridiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozmin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active formulation in a device of this invention. and that the use of the term "agent" or "drug" in no way excludes the use of two or more such agents or drugs.

The agents can be in various forms, such as unchanged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed.

The amount of active agent employed in the delivery device will be that amount necessary to deliver a therapeutically effective amount of the agent to achieve the desired result at the site of delivery. In practice, this will vary widely depending upon the particular agent, the side of delivery, the severity of the condition, and the desired therapeutic effect. Thus, it is not practical to define a particular range for the therapeutically effective amount of active agent incorporated into the device.

The hydrophillic polymeric material polymeric material useful herein may comprise, polysaccharides, methyl cellulose, sodium or calcium carboxylmethyl cellulose, hydroxypropylmethyl cellulose, hydroxypropyl cellulose, hydroxethyl cellulose, nitrocellulose, carboxymethyl cellulose and other cellulose ethers, and polyethylene oxides (eg. Polyox®, Union Carbide). Other materials useful as the hydrophillic polymeric material include but are not limited to methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (Eudrgit™) or other acrylic acid derivatives, sorbitan esters, natural gums, lecithins, pectin, alginates, ammonia alginate, sodium or potassium alginate, calcium alginate, propylene glycol alginate, potassium alginate, agar, gum arabic, gum karaya, locust bean gum, gum tragacanth, carrageenans, gum ghatti, guar gum, xanthan gum, scleroglucan, and blends of the above.

The pharmaceutically acceptable carrier useful herein may comprise more than one ingredient, such as, for example, a buffer, a viscosity regulating vehicle, a surfactant, a dye, a permeation enhancer, a proteinase inhibitor, or other formulation ingredients and additives, as are known in the art.

In addition to design of the active agent formulation to provide a specific drug delivery profile, the number, size, and placement of the insoluble bands that are applied onto the active agent formulation matrix may be varied to provide the desired drug delivery profile. For example, bands of from about 0.1 mm to about 12 mm in width, preferably between about 0.5 and 8 mm, may be applied onto the active formulation matrix surface. Further, between about 2 and 10 bands may be used, but generally between about 2 and 6 are affixed to the matrix. The bands may be placed at opposite ends of the matrix (ie, spaced about 8 to 12 mm apart). The insoluble material may be any material that is nontoxic, biologically inert, nonallergenic and nonirritating to body tissue, and that maintains its physical and chemical integrity; that is, the bands do not erode or degrade in the environment of use during he dispensing period. Insoluble materials from which the bands may be prepared include, for example, polyethylene, polystyrene, ethylene-vinyl acetate copolymers polycaprolactone and Hytrel® polyester elastomers (Du Pont). Additional banding materials include but are not limited to polysaccharides, cellulosics, powdered cellulose, microcrystalline cellulose, cellulose acetate, cellulose actetate pseudolatex (such as described in U.S. Pat. No. 5,024,842), cellulose acetate propionate, cellulose acetate butyrate, ethyl cellulose, ethyl cellulose pseudolatex (such as Surelease® as supplied by Colorcon, West Point, Pa. or Aquacoat® as supplied by FMC Corporation, Philadelphia, Pa.). nitrocellulose, polyactic acid, poly- glycolic acid, polylactide glycolide copolymers, collagen, polycaprolactone, polyvinyl alcohol, polyvinyl acetate, polyethylene vinylacetate, polyethylene terphtalate, polybutadiene styrene, polyisobutylene, polyisobutylene isoprene copolymer, polyvinyl chloride, polyvinyledene chloride-vinyl chloride copolymer, copolymers of acrylic acid and methacrylic acid esters, copolymers of methylmethacrylate and ethylacrylate, latex of acrylate esters (such as Edragit® supplied by RoöhmPharma, Weiterstadt, Germany), polypropylene, copolymers of propylene oxide and ethylene oxide, propylene oxide ethylene oxide block copolymers, ethylenevinyl alcohol copolymer, poly sulfone, ethylene vinylalcohol copolymer, polyxlylenes, polyamides, natural and synthetic waxes, paraffin, carnauba wax, petroleum wax, white or yellow bees wax, castor wax, candelilla wax, rice bran wax, microcrystalline wax, stearyl alcohol, cetyl alcohol, bleached shellac, estrified shellac, chitin, chitosan, silicas, polyalkoxysilanes, polydimethyl siloxane, polyethylene glycol-silicone elastomers, crosslinked gelatin, zein, electromagnetic irradiation crosslinked acrylics, silicones, or polyesters, thermally crosslinked acrylics, silicones, or polyesters, butadiene-styrene rubber, glycerol ester of partially dimerized rosin, glycerol ester of partially hydrogenated wood rosin, glycerol ester of tall oil rosin, glycerol ester of wood rosin, pentaerythritol ester of partially hydrogenated wood rosin, pentaerythritol ester of wood rosin, natural or synthetic terpene resin and blends of the above.

The banding materials often are also formulated with plasticizers, and optionally with wetting agents, surgactants, opacifiers, colorants, flavorants, taste-masking agents, and the like. Examples of typical plasticizers are as follows: polyhydric alcohols, polyethylene glycol, glycerol, propylene glycol, acetate esters, glycerol triacetate, triethyl citrate, acetyl triethyl citrate, glycerides, acetylated monoglycerides, oils, mineral oil, castor oil and the like.

The rate of release of the active agent from the active agent dosage form is predominantly controlled by erosion of the aqueous gel formed by contacting the matrix with the fluid environment of use. The drug released, m at time t, is proportional to the surface area of the system and can be written as $$dm/dt = KA \quad \text{(Equation 1)}$$

K is the erosion constant in mg/cm²hr and varies according to the molecular weight, particle size and hydrophilicity of the hydrophilic polymer of the matrix, the solubility of the drug in the environmental use, and the hydrodynamic condition of the erosive media.

A is the erosion area.

The release profile dm/dt is constant if K and A remain constant.

Substituting Equation 1 with the area of a cylindrical matrix with negligible end effects gives $$dm/dt = K2\pi RL \quad \text{(Equation 2)}$$

L is the length of the cylinder and
R is the radius of the cylinder at time t.
The mass release at time t is $$m = \pi[R_0^2 - R^2]LC_0 \quad \text{(Equation 3)}$$

$R_0$ is the initial radius of the cylinder and
$C_0$ is the initial concentration of the drug in the cylinder.
Substituting Equation 3 into Equation 2 leads to $$dR/dt = -K/C_0 \quad \text{(Equation 4)}$$

integrating Equation 4 gives $$R = R_0 - (K/C_0)t \quad \text{(Equation 5)}$$

The fraction amount of drug release, F, can now be defined by substituting Equation 5 into Equation 3 as follows $$F = m/m_0 = \pi[R_0^2 - R^2]LC_0) = 1 - [1 - Kt/(C_0R_0)]^2 \quad \text{(Equation 6)}$$

$$dF/dt = 2\ K/C_0R_0 - (2\ K^2/C_0^2R_0^2)t \quad \text{(Equation 7)}$$

Figure 7A:
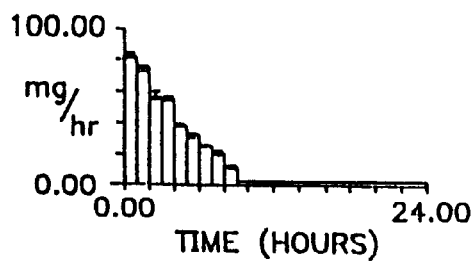
FIGS. 7A, 8A, 9A, 10A, and 11A show the release rates of the drugs from the devices while 7B, 8B, 9B, 10B and 11B show the cumulative doses of the drugs over a delivery period of up to 20 hours.
Figure 7B:
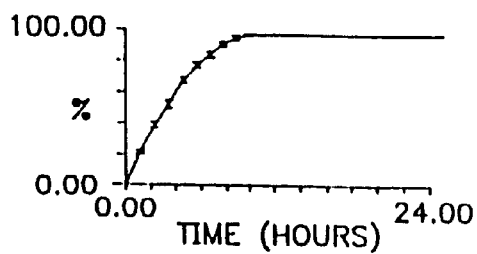
FIGS. 7, 8, 9, 10 and 11 (A and B) are graphs showing the performance of ibuprofen matrices with bands of varying number and placed in different positions on the matrices.

Equation 7 indicates that the plot of the rate of active agent released from a cylindrical dosage form without bands versus time will be linear and will decrease with time, as is shown in FIG. 7A. As drug is releases from an unbanded capsule, the diameter of the cylinder as well as the area of erosion decreases. In contrast, as the polymeric core of the banded cylinder of this invention shrinks, new surface area is created and exposed to the environment of use (see FIF. 2). As a result, the amount of active agent released over time may remain constant or may increase with time depending on the rate of the new surface area being generated. By arrangement of the number, size and location bands on the dosage form, the total new surface area created by erosion can be predicted and the desired release profile can be achieved.

The bands may be placed onto the surface of the matrix such that, as the matrix erodes, the bands become loose and drop off the matrix. These bands are easily excreted from the gastrointestinal tract. As the number of bands remaining on the surface of the matrix decreases, more matrix surface area will be exposed. The matrix will therefore erode in a fashion that approaches zero order.

The bands may also be printed onto the surface of the matrix. The matrix will erode where not covered by the bands as described above with reference to FIGS. 1–5.

In order to prepare a device of the present invention, the active agent formulation is first prepared and formed into a matrix of the desired size and shape. The matrix in its initial prepared form is about the size and dimensions of a size "5" to size "OOO" hard gelatin capsule. The cross-sectional shape of the matrix may be circular or may be oval, triangular, square, hexagonal or other shapes that are easily handled, especially by patients with limited dexterity. The rings or bands are then placed onto the surface of active agent formulation matrix or printed onto the surface using conventional banding or printing techniques.

Figure 6:
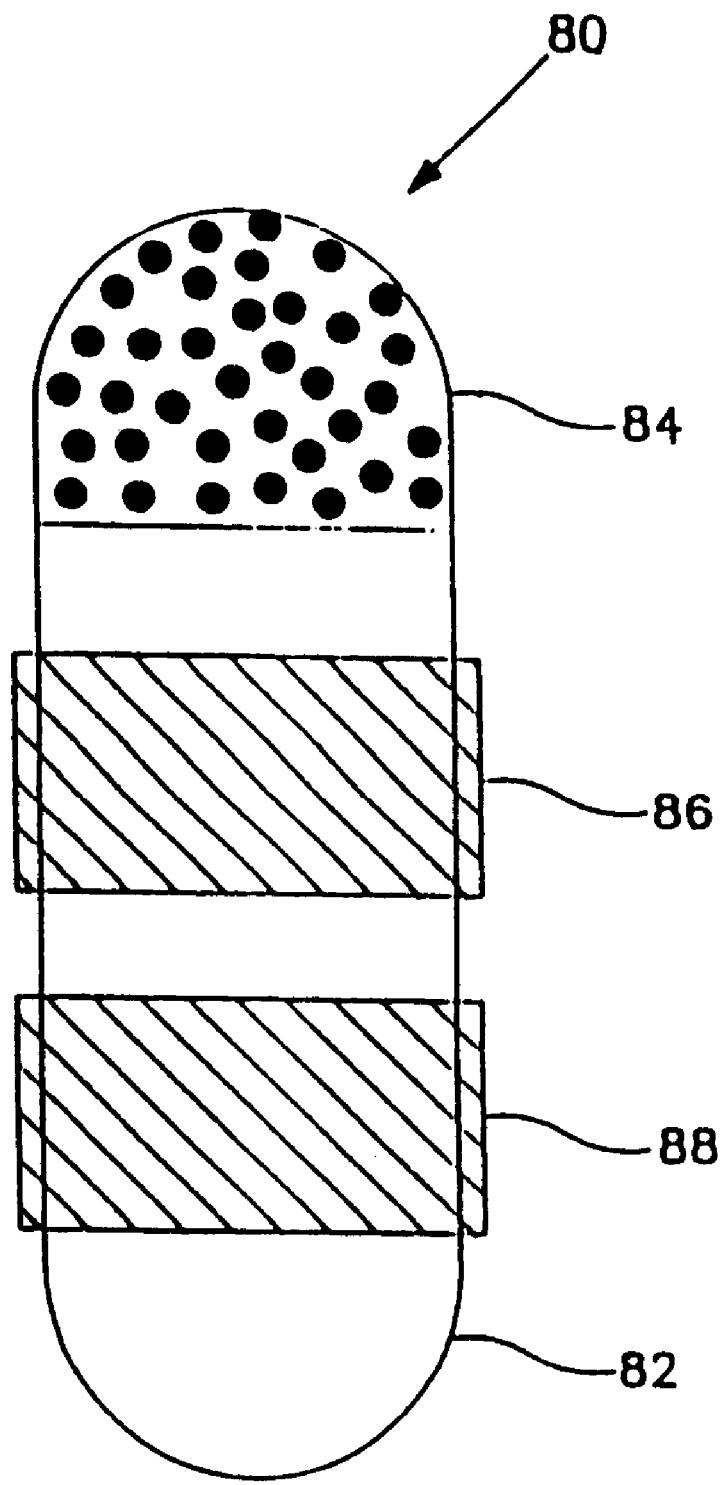
FIG. 6 is a side elevational view of a third embodiment of the delivery device of the present invention, the device being in prepared form prior to placement in the environment of use.

In addition to the devices described above, embodiments are contemplated that include non-uniform matrices. These devices include matrices with two or more active agents or two or more pharmaceutically acceptable carriers. An example of a device 80 with a non-uniform matrix is shown in FIG. 6. A lower portion 82 of the matrix material is formed from the hydrophilic polymeric materials described above that erode over time upon exposure to a fluid environment of use. An upper portion 84 of the matrix material disintegrates upon placement in the fluid environment of use. The latter portion of the matrix will provide for an initial pulse of active agent as the material swells and separates from the rest of the matrix. The remaining portion of the device, with bands 86 and 88 as described above, will provide for the prolonged delivery of the same or a different active agent. Materials that swell and disintegrate upon placement in the fluid environment of use include, but are not limited to hydroxypropyl cellulose having a hydroxypropoxl content of 7 to 16 weight percent, crosslinked polyvinyl pyrrolidone, crosslinked starch, microcrystalline cellulose, chitin, cellulose fiber and the like.

The following examples are illustrative of the present invention. They are not to be construed as limiting the scope of the invention. Variations and equivalents of these examples will be apparent to those skilled in the art in light of the present disclosure, the drawings and the claims herein.

EXAMPLE 1

A delivery device according to the present invention was prepared as follows, 58 grams of the analgesic drug, ibuprofen, 25 grams of hydroxypropyl methylcellulose having a number average molecular weight of 9,200 grams per mole, and 15 grams of hydroxypropyl methylcellulose having a molecular weight of 242,000 grams per mole, were passed through a screen having a mesh size of 40 wires per inch. The celluloses each had an average hydroxyl content of 8 weight percent and an average methoxyl content of 22 weight percent. The resulting sized powders were tumble mixed. Anhydrous ethyl alcohol was added slowly to the mixed powders with stirring until a dough consistency was produced. The damp mass was the extruded through a 20 mesh screen and air dried overnight. The resulting dried material was re-screened through a 20 mesh screen to form the final granules. 2 grams of the tabletting lubricant, magnesium stearate, which had been sized through an 80 mesh screen, was then tumbled into the granules.

690 mg of the resulting granulation was placed in a die cavity having an inside diameter of 9/32 inch and compressed with deep concave punch tooling using a pressure head of 2 tons. This formed a longitudinal capsule core having an overall length, including the rounded ends, of 0.691 inch. The cylindrical body of the capsule, from tablet land to tablet land, spanned a distance of 12 mm. Each core contained a unit dose of drug 400 mg. Rings of polyethylene having an inside diameter of 9/32 inch, a wall thickness of .013 inch, and a width of 2 mm were then fabricated. These rings, or bands, were press fitted onto the capsule to complete the dosage form.

EXAMPLE 2

Drug release studies were performed by placing the dosage forms in a slotted basket. The inside diameter of the basket was 14 mm and the length was 50 mm. The basket was attached to a reciprocating motor. The basket was then immersed in 50 ml of simulated intestinal fluid at 37° C., and shaken vertically in the media with a amplitude of 3.8 cm and a frequency of 99–101 cycles per minute. After 1 hour of shaking, the basket was transferred to a fresh 50 ml volume of the test media. This procedure was continued, hour by hour, for nine hours. The systems then were allowed to release continuously for another 13 hours to complete a 24 hour test duration. The release receptor solutions were then analyzed for drug content by ultraviolet spectroscopy. The release rate as a function of time and cumulative release as a function of time were computed.

Figure 8A:
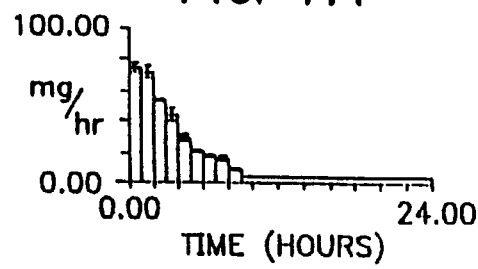
Figure 8B:
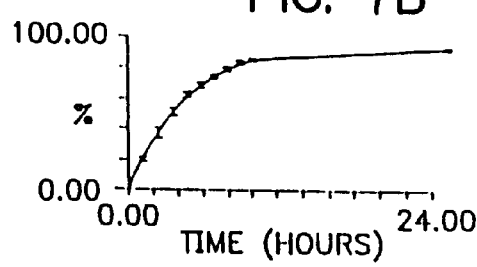
Figure 9A:
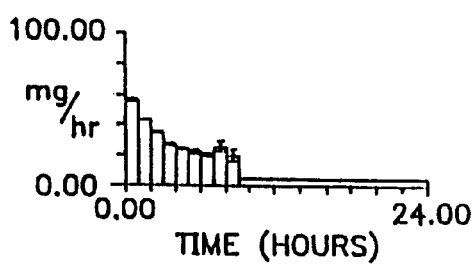
Figure 9B:
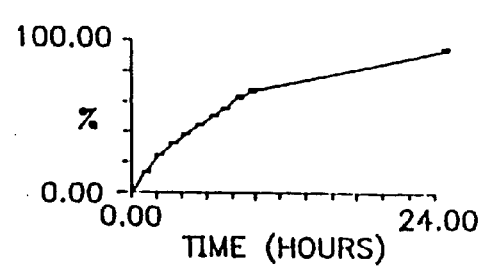
Figure 10A:
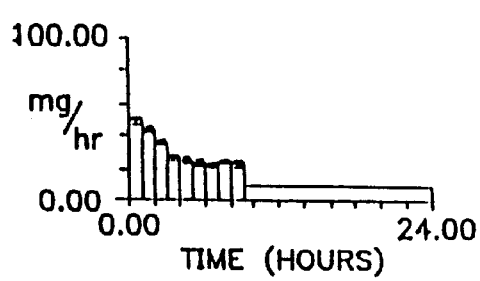
Figure 10B:
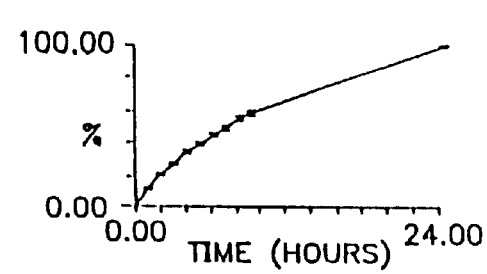

FIGS. 7–10A show the release of he ibuprofen cylindrical matrix formulation described in Example 1 and FIGS. 7–10B show the cumulative amount of drug released, FIGS. 7A and B show the 0.281 inch by 0.691 inch longitudinal capsule with no bands, FIGS. 8A and B show the capsule with one 2 mm band positioned in the middle of the capsule. FIGS. 9A and B show the capsule with two 2 mm bands one positioned at each end of the capsule with an 8 mm distance between the bands, FIGS. 10A and B show the capsule with three 2 mm bands, one positioned in the middle of the capsule and one positioned at each end with a distance of 3 mm between the bands. The delivery rate approaches zero order as greater numbers of bands are included. Further, as more of the surface area is covered by the insoluble material, the release rate is prolonged. The total delivery times to release 90% of the initial dose are as follows: for no bands, 6.6 hours; for one 2 mm band, 10.7 hours: for two 2 mm bands, 17.6 hours; and for three 2 mm bands, 19.2 hours.

EXAMPLE 3

Figure 11A:
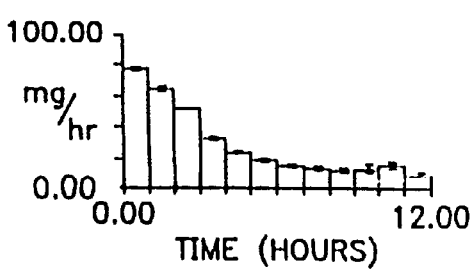
Figure 11B:
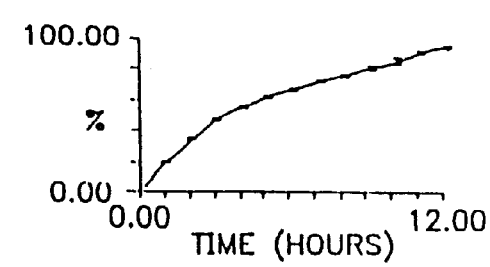

FIG. 11 A shows the release rate as a function of time of the ibuprofen cylindrical matrix formulation described in Example 1 except that the system banded with two rings was tested with a different positioning of the rings. FIG. 11B shows the corresponding cumulative release versus time. The two rings were positioned such that they were equisapced along the 12 mm cylindrical body, with 2.7 mm between the land and the ring, and 2.7 mm between the rings. A comparison of these patterns with the patterns illustrated in FIGS. 9A and 9B, demonstrates that different patterns can be achieved with different ring configurations. The total delivery time to deliver 90% of the dose is 10.2 hours rather than 17.6 hours.

EXAMPLE 4

A fast-release drug granulation was prepared as follows; 87 grams of ibuprofen, 10 grams of hydroxypropyl cellulose having a hydroxypropoxl content of 11 weight percent, and 1 gram of hydroxypropyl methyl cellulose having a hydroxypropoxyl content of 8 weight percent and a methoxy content of 22 weight percent and having a number average molecular weight of 9,200 grams per mole, were screened through a 40 mesh sieve. The sized powders were mixed and anhydrous ethanol was added with stirring until a uniform, damp mass was produced. The mixture was extruded through a 20 mesh sieve. The elongated granules produced were air dried. The dried granules were re-screened through a 20 mesh sieve. 2 grams of stearic acid which had been passed through an 80 mesh sieve were tumble mixed into the granules for 3 minutes.

690 mg of the granualtion of Example 1 were filled into a die cavity having an inside diameter of 9/32 inch and lightly compressed with deep concave punch tooling. The upper punch was removed and 230 mg of the fast-release granulation was placed on the lightly compressed core. The upper punch was returned to the die cavity and a 2 ton compression force was applied, thereby forming a two-layered tablet. Two rings were press fitted onto the 690 mg portion of the dosage form according to the procedures specified in Example 3.

An abrasion resistant, protective coating was applied to the banded, two-layered tablet as follows. A coating solution was prepared by dissolving 63 grams of hydroxypropyl methylcellulose having a hydroxyproproxyl content of 10 weight percent and a methoxy content of 29 weight percent with a number average molecular weight of 11,900 grams per mole, and 7 grams of polyethylene glycol having a molecular weight of 3,350 grams per mole, in 930 grams of water. The ringed tablets were then placed in a pan coating machine. The coating solution was sprayed onto the ringed tablet in a current of warmed air until 40 mg of film were deposited on each tablet.

The resulting two-layer, film coated systems were tested for release of drug according to the procedures describe in Example 2, except that the release test media was simulated gastric fluid having a pH of approximately 1.2. In this test, the fast-release layer dispensed 200 mg of ibuprofen within 10 minutes, and the remaining 400 mg dose was dispensed slowly according to the release characteristics specified in Example 3.

78 grams of ibuprofen and 20 grams of hydroxypropyl-methylcellulose having a number average molecular weight of 9,200 grams per mole and a hydroxyl content of 8 wt% and a methoxyl content of 22 wt% were passed through a 40 mesh screen. The resulting sized powders were tumble mixed. Anhydrous ethyl alcohol was added slowly to the powders with stirring until a dough consistency was produced. The damp mass was then extruded through a 20 mesh screen and air dried overnight. The resulting dried material was then rescreened through a 20 mesh screen to form the final granules. 2 grams of tabletting lubricant, stearic acid, which had been sized through an 80 mesh screen, were then tumbled into the granules.

513mg of the resulting granulation was placed in a die cavity having an inside diameter of 9/32 inch and compressed with a deep concave punch tooling using a pressure head of 2 tons, forming a longitudinal capsule having an overall length, including the rounded ends, of 0.543 inch. The cylindrical body of the capsule, from tablet land to tablet land, spanned a distance of 9 mm. Each capsule contained a unit dose of drug of 400 mg. Rings of polyethylene having an inside diameter of 9/32, a wall thickness of 0.013 inch, and a width of 2 mm were then fabricated. These rings or bands were pressed fitted onto the capsule to complete the dosage form.

Figure 12:
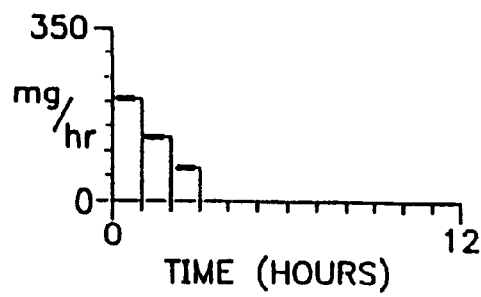
FIGS. 12, 13, 14 and 15 are graphs showing the release rates of ibuprofen matrices with bands of varying number for a period of up to 4 hours.
Figure 13:
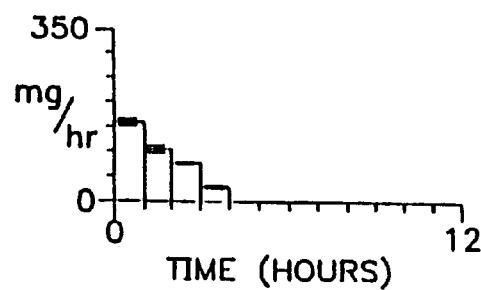
Figure 14:
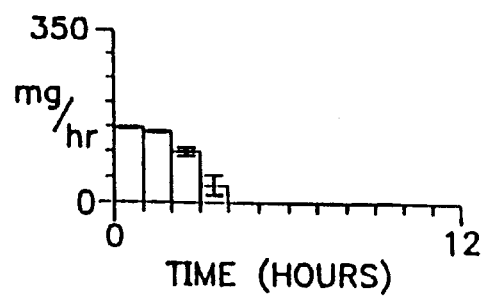
Figure 15:
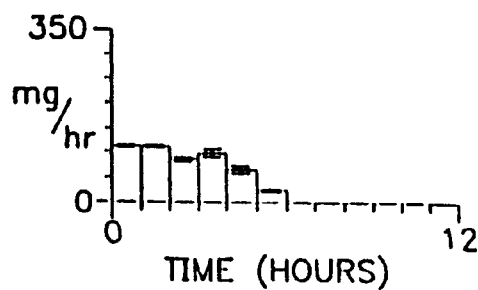

Drug release studies were performed as described in Example 2. FIGS. 12–15 show the rates of the ibuprofen cylindrical matrix formulation described above. FIG 12 shows the release rate of the matrix with no bands. FIG. 13 shows the matrix with two 2 mm bands positioned in the middle of the matrix with a distance of 2 mm between the bands. FIG. 14 shows the matrix with three 2 mm bands, one positioned in the middle of the capsule and one positioned at each end with a distance of 2 mm between the bands. FIG. 15 shows the matrix with four 2 mm bands, one positioned at each end and two positioned in the middle, each separated by a distance of 0.33 mm.

As noted on the previous example, the delivery rates shown in FIGS. 12–15 approach zero order as greater numbers of bands are included. Further, as more of the surface area is covered by the insoluble material, the release rate is prolonged. The total delivery times to dispense 90% of the initial dose are as follows: for no bands, 2.3 hours; for two bands, 2.8 hours; for three bands 2.8 hours; and for four bands, 3.7 hours.

EXAMPLE 6

A 550 mg unit dose for prolonged release of the analgesic drug actaminophen is prepared as follows. 78 grams of acetaminophen are passed through a sizing screen having 40 wires per inch. 20 grams of a hydroxypropyl methylcellulose having a hydroxypropyl content of 8 wt %, a methoxyl content of 22 wt %, and a number average molecular weight of 27,800 grams per mole are passed through a sizing screen with 100 wires per inch. The sized powders are tumble mixed for 5 minutes. Anhydrous ethanol is added to the mixture with stirring until a damp mass is formed. The damp mass is passed through a sizing screen with 20 wires per inch. The resulting damp granules are air dried overnight, and then passed again through the 20 mesh sieve. 2 grams of the tabletting lubricant, magnesium stearate are passed through a sizing screen with 80 wires per inch. The sized magnesium stearate is blended into the dried granules to form the final granulation.

705 mg portions of the final granulation are placed in die cavities having inside diameters of 0.281 inch. The portions are compressed with deep concave punches under a pressure head of 1 ton, forming longitudinal capsule-shaped tablets.

The capsules are fed into a Tait Capsealer Machine (Tait Design and Machine Co., Manheim, Pa.) where three bands are printed onto each capsule. The material forming the bands in a mixture of 50 wt % ethylcellulose dispersion (Surelease®, Colorcon, West Point, Pa.) and 50 wt % ethyl acrylate methylmethacrylate (Eudragit® NE 30D, RöhmPharma, Weiterstadt, Germany). The bands are applied as an aqueous dispersion and the excess water is driven off in a current of warm air. The diameter of the bands is 2 millimeters.

The above description has been given for ease of understanding only. No unnecessary limitations should be understood therefrom, as modifications will be obvious to those skilled in the art.

What is claimed is:

1. An active agent delivery device for use in a fluid environment, comprising:

an active matrix, said active agent matrix including an active agent in admixture with a pharmaceutically acceptable carrier; and at least two bands coupled to said active agent matrix, said at least two bands being insoluble in the fluid environment and being adapted to temporarily isolate a first portion of said active matrix from the fluid environment;

wherein when the active agent delivery device is placed in the fluid environment, a second portion of said active agent matrix erodes, thereby increasing a surface area of said active agent matrix that is in contact with the fluid environmment.

2. The active agent delivery of claim 1, wherein erosion of said active agent matrix continues until said active agent matrix has been completely eroded from said at least two bands.

3. An active agent delivery device for use in a fluid environment, comprising:

an active agent matrix, said active agent matrix including an active agent in admixture with a pharmaceutically acceptable carrier;

at least two bands coupled to said active agent matrix, said at least two bands being insoluble in the fluid environment and being adapted to temporarily isolate a portion of said active agent matrix from the fluid environment;

wherein a rate of release of said active agent matrix into the fluid environment increases with time as a surface area of said active agent matrix that is in contact with the fluid environment increases.

4. An active agent delivery device, comprising:

an active agent matrix formed into an oblong shape, said active agent matrix having a longitudinal axis;

an insoluble ring concentrically surrounding said active agent matrix, wherein a central axis of said ring coincides with the longitudinal axis of said active agent matrix;

wherein upon placement of the active agent delivery device into a fluid medium, said active agent matrix begins to erode.

5. The active agent delivery device of claim 4, wherein as said active agent matrix erodes, said ring loosens and separates from said active agent matrix.

6. The active agent delivery device of claim 5, wherein a surface area of said active agent matrix that is exposed to the fluid medium increases as said ring separates from said active agent matrix.

7. An active agent delivery device for use in a fluid medium, comprising:

an active agent matrix formed into a cylindrical shape;

at least two rings coupled to said active agent matrix, said at least two rings being insoluble in the fluid medium and being adapted to temporarily isolate a portion of said active agent matrix from the fluid medium;

wherein upon placement of the active agent delivery device into the fluid medium, said active agent matrix begins to erode, causing said rings to loosen and separate from said active agent matrix.

8. The active agent delivery of claim 7, wherein as the number of rings remaining on said active agent matrix decreases, a surface area of said active agent matrix that is exposed to the fluid medium increases, thereby causing said active agent matrix to erode in a fashion that approaches zero order.

9. The active agent delivery device of claim 8, wherein a spacing of said at least two rings on said active agent matrix is non-uniform.

10. An active agent delivery device, comprising:

an active agent matrix formed into an oblong shape, said active agent matrix having a longitudinal axis;

a number N (where N is a whole number greater than one) insoluble rings concentrically surrounding said active agent matrix, wherein a central axis of said rings coincides with the longitudinal axis of said active agent matrix;

wherein upon placement of the active agent delivery device into a fluid medium and upon sufficient erosion of said active agent matrix between said N insoluble rings, the active delivery device separates into a number N pieces.

11. The active agent delivery device of claim 10, wherein the number N of insoluble rings is between 2 and 10 inclusive.

12. The active agent delivery device of claim 11, wherein the number N of insoluble rings is between 2 and 6 inclusive.

13. The active agent delivery device of claim 1, wherein a width of each of said at least two bands is different.

14. The active agent delivery device of claim 1, wherein a width of each of said at least two bands is substantially the same.

15. The active agent delivery device of claim 3, wherein a width of each of said at least two bands is different.

16. The active agent delivery device of claim 3, wherein a width of each of said at least two bands is substantially the same.

17. The active agent delivery device of claim 7, wherein a width of each of said at least two rings is different.

18. The active delivery device of claim 7, wherein a width of each of said at least two rings is substantially the same.

* * * * *